June 23, 1936. W. SPANDIKOW, JR Plant Pat. 187
ROSE PLANT
Filed July 20, 1935
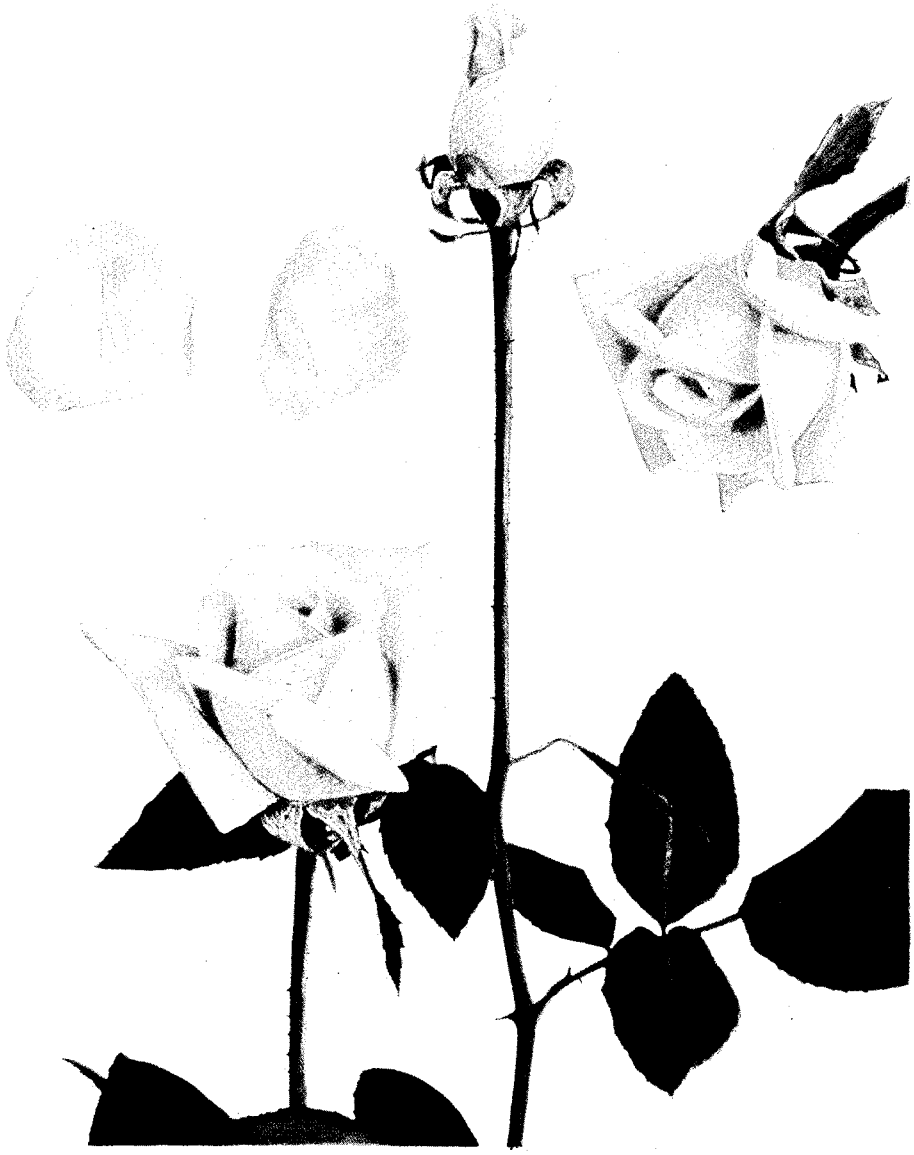
Inventor,
William Spandikow Jr,
Rummler, Rummler & Woodworth
Attys.

Patented June 23, 1936

Plant Pat. 187

UNITED STATES PATENT OFFICE

187

ROSE PLANT

William Spandikow, Jr., Maywood, Ill.

Application July 20, 1935, Serial No. 32,410

1 Claim. (Cl. 47—61)

This invention relates to roses and the purpose in the production of the new variety is to attain a rose of distinctive beauty and responding to the author's concept as to essential characteristics for commercial use, such as straightness and strength of stem, uniformity in size and coloring of the bloom, capacity for quantity production and for withstanding a reasonable amount of handling in packing, shipment, and use. In this regard, the product has many desirable qualities.

It is distinguishable from all other roses by having rich pink and bright canary or quince yellow colors at the base of the corolla blending into a mild pink tinged silvery mass, giving generally a waxy, opaque, artificial effect. Another characteristic is the peculiar faint tracing of pink veins curving outwardly from the center of the petals.

The bloom differs from the Jonkheer J. L. Mock noticeably in the fact that the latter has a more solid pink color with a silver sheen and does not open well in winter months. Radiance is another more solid pink rose having a tendency to turn blue and is more globular in the fall and winter.

The new plant was first produced in 1930 from seeds of a rose plant known as the Mrs. Charles Russell which was crossed by pollen from the Madam Butterfly rose. Continuous asexual reproduction of the same plant has been effected since that time by budding and extensive grafting on to wild rose stock.

The new plant is distinguishable from either parent by being less prolific than the Madame Butterfly but more so than the Mrs. Charles Russell. It has heavier and darker foliage than either parent and it appears to be freer from black spot and other diseases than either parent.

The bloom in midwinter greenhouse productions is from three and one-half to four inches in diameter and the buds measure from two to two and one-half inches in height.

The number of petals is from 35 to 40 and they are straighter or less curved than either of the parents. The unfolded part of a bloom is distinctly spiral when viewed from above. The petals hold firmly to the flower and the latter will stand considerable rough handling.

The stems are exceptionally heavy and straight.

The bud is decidedly larger than that of the Madam Butterfly rose which the new flower resembles much more than the Mrs. Charles Russell.

Classification:—Hybrid tea rose

Flower:—

*Blooming habit.*—Everblooming, having an annual production of about 15 blooms per plant in a greenhouse at Maywood, Ill.

Bud:—

Is large and pointed; is not affected by wet or hot weather.

*Color.*—When the petals first divide is pink; when the petals begin to unfurl the color thereof is moonlight or flesh natural (Plate 11–A–2) with canary yellow (Plate 11–L–3) at the base; when half blown, the insides of the petals are moonlight or flesh natural (Plate 11–A–2) and the reverse sides of the petals are also moonlight or flesh natural (Plate 11–A–2) of a deeper hue.

*Sepals.*—Serrated and curl back in developing.

*Calyx.*—Shape—round. Size—large. Aspect—smooth. Odor when rubbed—same as foliage.

*Peduncle.*—Of medium length. Aspect—rough or prickly. Color—medium green—and is stiff, erect and heavy.

The bud opens well and is not affected by adverse conditions.

Bloom:—

*Size.*—Very large, averaging from 3½ to 4 inches when fully expanded. It is borne singly on long and strong stems and has a high center. It has a tendency to flatten out as it ages.

*Petalage.*—30 to 35 petals under normal conditions.

*Color.*—The general color of the bloom is a cameo pink (Plate 50–C–2) and a deeper pink (Plate 41–H–1) toward the center of the bloom. The color at the base of the inside and the outside of the petals includes areas of canary yellow (Plate 11–L–3) blending into the pink.

The general hue on the outside of the petal is much like the cameo pink corresponding to the general tonality of the bloom from a distance. The cameo color of the bloom does not noticeably change at the end of the first, second or third day after the flower opens.

The color at the base of the inside of the petal is a canary or quince yellow which blends on the inside of the petal to a warm pink. The hue on the outside of the petal is a cameo pink. Where the petal curls or folds over, there is what is sometimes termed a "moonlight" tone, such as shown on plate 11–A–2.

*Petals.*—Texture—thick and not affected by wet or hot weather; are shiny on the inside and outside; of oval form and are regularly arranged. Pentaloids—are few. Persistence—hang on and dry. Fragrance—the bloom has little or no noticeable fragrance.

The lastingness of the bloom on the plant and as a cut flower is very long.

Sexual Organs:—
*Stamens.*—Large and many of them.
*Color.*—White.
*Pollen.*—Golden yellow.
*Styles.*—Bunched.
*Stigmas.*—White.
*Ovaries.*—Some protrude from calyx.
Fruit:—
Is sterile with its own pollen, having a round form or somewhat gourd-shaped with the seeds protruding.
*Aspect.*—Smooth—and the color russet-brown.
*Sepals.*—Permanent.

*Plant*

Form:—
The plant is a bush of medium growth.
Foliage:—
*Leaflets.*—5.
*Size.*—Large.
*Quantity.*—normal.
*Color.*—Light green on both upper and lower sides. Old foliage is dark green on the upper and lower sides.
*Texture.*—Upper side, leathery. Under side, rough.
*Ribs and veins.*—Prominent.
*Edge.*—Serrated.
Leaf stem color is green.
*Stipules.*—Serrated.
The plant is disease resistant so far as known.
Wood:—
New wood is reddish in color and the bark is smooth. Old wood is green in color and has a smooth bark.
Thorns:—
On the main stalk and laterals are many and in form have a broad base; are long and hooked downward.
*Color when young.*—Transparent and irregular in position.
Prickles are numerous on the main stalks and laterals.
Short needles—numerous on the main stalks and laterals.

Other distinguishing characteristics of the plant are the long stems; its upright growth and its ability to stand a fair amount of forcing.

The new variety of rose may be further identified by reference to the accompanying permanently colored photographic illustration thereof. The slight waxy, or artificial, appearance is somewhat intensified when the bloom is in an artificial light.

The plants bloom continuously having an annual production of about fifteen blooms per plant but the time of development of the individual blooms, measured between cuttings or pinchings, is faster than either parent by ten or twelve days. The blooms have long stems from above the pinch and in this respect are like the Russell parent plant. The blooms open well, have a slight fragrance, and the petals do not fall off.

All reference to color in the description of this new variety of rose is based on Maerz & Paul's "Dictionary of Color", edition of 1930.

I claim:

A rose plant produced by hybridization of the Mrs. Charles Russell and Madame Butterfly roses which is distinguishable from other varieties by its opaque, somewhat waxy appearance and mildly pinkish, silvery white general color which is modulated by strong canary yellow and pink areas near the base of the petals.

WILLIAM SPANDIKOW, JR.